United States Patent
Wagner et al.

(10) Patent No.: US 6,840,124 B2
(45) Date of Patent: Jan. 11, 2005

(54) SCREENING PROCESS FOR THE PRODUCTION AND CHARACTERIZATION OF POLYURETHANE FOAM MATERIALS

(75) Inventors: Joachim Wagner, Köln (DE); Peter Jähn, Leverkusen (DE); Jacqueline Kusan-Bindels, Neuss (DE); Dagmar Ulbrich, Köln (DE); Rolf Albach, Köln (DE); Hermann-Josef Kirschbaum, Kerpen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 51 days.

(21) Appl. No.: 10/373,615

(22) Filed: Feb. 24, 2003

(65) Prior Publication Data

US 2003/0159531 A1 Aug. 28, 2003

(30) Foreign Application Priority Data

Feb. 28, 2002 (DE) .......................... 102 08 952

(51) Int. Cl.[7] .............................................. G01N 33/44
(52) U.S. Cl. ............................ 73/866; 73/149; 73/863; 73/863.31; 73/863.33; 436/174; 521/155; 521/170
(58) Field of Search ................................. 521/155, 170; 73/149, 863, 863.31, 863.33, 866; 436/174

(56) References Cited

U.S. PATENT DOCUMENTS

| | | | |
|---|---|---|---|
| 4,272,049 A | | 6/1981 | Kindel .................... 249/83 |
| 4,988,271 A | | 1/1991 | Kumasaka et al. |
| 5,154,088 A | * | 10/1992 | Lehnert et al. ............... 73/866 |
| 6,037,180 A | * | 3/2000 | Yorkgitis et al. ............ 436/56 |
| 6,221,929 B1 | * | 4/2001 | Ryugo et al. ............... 521/114 |
| 6,235,799 B1 | | 5/2001 | Eisen et al. ................... 521/51 |
| 6,294,388 B1 | * | 9/2001 | Petro ............................ 436/8 |

FOREIGN PATENT DOCUMENTS

| | | |
|---|---|---|
| DE | 28 35 038 | 2/1980 |
| DE | 30 01 602 | 7/1980 |
| DE | 156 873 | 9/1982 |
| DE | 42 30 068 | 3/1994 |
| DE | 197 01 074 | 7/1998 |
| DE | 198 10 092 | 9/1999 |
| DE | 198 54 837 | 5/2000 |
| DE | 197 30 891 | 8/2000 |
| DE | 199 60 779 | 7/2001 |
| DE | 100 28 226 | 12/2001 |
| DE | 197 43 590 | 1/2002 |
| EP | 1 176 413 | 1/2002 |
| FR | 2 447 030 | 1/1980 |
| FR | 2 804 898 | 8/2001 |
| WO | 00/70323 | 11/2000 |

OTHER PUBLICATIONS

Mathematical Modelling In Materials Processing, Oxford University Press, (month unavailable) 1991, pp. 399–417 L. Lefebvre and R. Keunings "Mathematical Modelling and Computer Simulation of the Flow of Chemically–Reacting Polymeric Foams".

* cited by examiner

*Primary Examiner*—John M. Cooney, Jr.
(74) *Attorney, Agent, or Firm*—Joseph C. Gil; Lyndanne M. Whalen

(57) ABSTRACT

Rapid and efficient production and examination of formulations for polyurethane foams using only small amounts of materials are achieved by allowing the foam-forming mixture to foam in a container, preparing disks from sections of the container in which the foam is present and removing a plurality of cylindrical samples having substantially the same density from the disk.

1 Claim, No Drawings

SCREENING PROCESS FOR THE PRODUCTION AND CHARACTERIZATION OF POLYURETHANE FOAM MATERIALS

BACKGROUND OF THE INVENTION

The present invention provides a process for the rapid and efficient production and examination of polyurethane ("PU") foam-forming formulations in which only a small amount of material is required.

Screening of PU foam formulations is generally carried out by hand. Laboratory packets containing from 200 to 300 g of foam are produced after all of the ingredients have been manually weighed, mixed together in a bench stirrer, and the mixture has been poured into paper packets. Disadvantages of this manual screening are the low maximum throughput of 15 packets per day per technician, poor reproducibility resulting from the non-documenting of errors/deviations in weighing, stirring times, stirrer speed, etc., and a laborious determination by hand of reaction parameters such as the cream time, full rise time, fiber time and tack-free time.

A problem when conducting physical testing of PU foams is that the removal of a plurality of identical sample bodies in accordance with the DIN standard (sample size at least 125 $cm^3$) is virtually impossible due to flow distance phenomena and fluctuations in density (up to 10%) and to the limited sample quantity from one identical batch. Additionally, destructive testing techniques frequently also mean that the sample body can be used only for a single measurement thereby necessitating the use of a plurality of packets which are as nearly identical as possible but which may frequently have properties which differ from one another (for example, differences in densities or in open cell content). Defined storage times must be observed before the samples are examined, in order to avoid or standardize ageing of the samples due to cell gas exchange.

SUMMARY OF THE INVENTION

A process has now been developed which enables the time taken and material consumed in the screening of formulations for polyurethane foams to be greatly reduced and moreover enables the reliability and reproducibility of the measured data obtained to be increased. This is accomplished by foaming a relatively small amount of foam-forming mixture in a container and cutting the container in which the foam is present into one or more disks or some other desired shape having the desired thickness. The desired number of samples are then bored out the foam-containing portion of the container for testing.

DETAILED DESCRIPTION OF THE INVENTION

In the process of the present invention, from 10 to 50 g, preferably from 10 to 20 g, most preferably about 16 g, of the polyurethane-forming formulation to be tested are introduced into a sealable container having a volume of from 10 to 1000 ml, preferably from 125 to 500 ml, which container is composed of a gas-tight material (for example, polypropylene (PP), polyethylene (PE) or polystyrene (PS)). For this purpose, the individual components of the foam-forming formulation are preferably weighed into and mixed in the container. However, the reaction mixture may also be charged ready for use into the container. The container is preferably in a form such as that of a cylindrical beaker having the flattest possible base. Weighing is preferably conducted With an automated computer-controlled metering station such as that described in German Patent Application No. 101 59 272.8. After weighing or after the foaming operation is complete, the container is sealed in a manner which renders it gas-tight with a lid made of the same material as the container, thus preventing any exchange of the cell gas in the PU foam and the ingress of air. Since ageing of the samples is in this way suppressed, even after a protracted storage time of approximately 6 months, no false values are obtained when physical examination of the sample(s) is carried out.

The foam-containing container is preferably made of a transparent or translucent material to enable optical measurement of important parameters such as rise height, cream time and/or full rise time during the foaming operation. These measurements may be performed, for example, by a video camera with on-line image evaluation, such as is described in, for example, L. Lefebvre and R. Keunings: "Mathematical Modelling and Computer Simulation of the Flow of Chemically-Reacting Polymeric Foams", in M. Cross et al. (Ed.): "Mathematical Modelling in Materials Processing", Oxford University Press, 1991, pp. 399–417.

At a defined distance from the base of the container, parallel to the base plane (or orthogonal to the sheath plane), the foam-filled containers are divided into disks of defined thickness in order to produce sample bodies, taking care not to give rise to scoring and striation of the surface. This may be accomplished by using, for example, a bandsaw having a narrow, deep sawing band with the highest possible number of teeth per cm and having set teeth. Sample thicknesses of from approximately 10 mm to 30 mm, preferably from 10 mm to 20 mm, and most preferably about 10 mm, have proven valuable. In order to minimize the influence exerted on the measured values by cells which have become cut open, it is important that the sample bodies have smooth surfaces. The sample preparations must also be carried out in a manner such that the cell walls are cut smoothly and do not break away during the preparation, thereby destroying lower cell layers.

Sample bodies for physical examination are prepared from a disk by boring out a plurality, preferably from 2 to 8, most preferably 4, of cylinders, in each case at the same distance from the central point (or from the edge) of the disk, using a hollow borer. Concentrically occurring variations in density are thus identical in all of the cylinders. A cylinder diameter of from 10 to 20 mm, preferably about 10 mm, has proven valuable. It is important that the cylinders be drilled in cutting manner, not punched, because impairment of the surface of the sample otherwise occurs. (See discussion above.)

In the next step of the process of the present invention, the dimensions (height, diameter) and the weight of the cylinders are checked to ensure that the densities of the sample bodies are identical to within a tolerance of 2%, preferably of less than 1%. If this is the case, the sample bodies are used in order to determine physical data of the foam which is to be tested. The open cell content, compressive strength, thermal conductivity, dimensional stability under conditions of hot or cold ageing can, for example, be determined by conventional measuring instruments and/or automated data acquisition. A crucial advantage of the process according to the invention is that as a result of the preparation of sample bodies having identical properties a plurality of different parameters can be determined in simultaneous and parallel manner from one polymer batch.

A plurality of disks of different density may be examined in order to determine a dependence of the physical properties on the density with a PU formulation which in other respects is identical.

Having thus described the invention, the following Example is given as being illustrative thereof.

EXAMPLE

In order to prepare a polyol formulation, 5.81 g of a polypropoxy ether having a hydroxyl number of 460 mg KOH/g, a functionality of 3 and a number average molecular weight of 370 g/mol, 0.44 g tris(1-chloro-2-propyl) phosphate, 0.09 g of a polyether siloxane stabilizer (Niax® SR242, OSI Specialties Germany GmbH), 0.12 g water, and 0.06 g dimethyl cyclohexylamine as a catalyst were metered into a 15 cm-high cylindrical PE synthesis container 6.9 cm in diameter (volume=500 ml), and mixed together. 0.61 g cyclopentane as the blowing gas and 8.87 g diphenylmethyl diisocyanate (MDI) containing 31 wt. % NCO groups, 38 wt. % 4,4'-, 2,4'- and 2,2'-isomers and 62 wt. % polynuclear MDI oligomers were then mixed into this polyol formulation. After this mixing, the foaming reaction to give a rigid polyurethane foam commenced. The PE synthesis container was not sealed.

The foam produced from the above-described 16 g reaction mixture along with its PE synthesis container was cut up on a bandsaw (model BS 400 E, Fried. Aug. Arnz "Flott" GmbH & Co., D-42857 Remscheid, saw blade 0.7 mm thick, 6.25 mm deep, 10 teeth/cm). The lower part of the foam cylinder (thickness of 2 cm) was discarded. The remaining material (above the discarded lower part of the cylinder) was divided into 1 cm-thick disks.

At a distance of 1.8 cm from the central point of each disk, 5 cylinders 1 cm in diameter were cut at heights of from 3 cm to 10 cm (lower edge). A boring cylinder of internal diameter 1 cm, similar to a cork borer but of hardened stainless steel and having an integrated ejector, was used for this purpose in order not to compress the foam as it was pressed out. The diameter and thickness of the cylinders as well as their weight were measured, and the density of the cylinders was calculated from them. The open cell content and compressive strength of the foam were determined on the cylinders which were identical to within the tolerance.

The open cell content of the foam was determined by way of gas displacement processes (pycnometry). Here, the sample volume which is obtainable when low gas pressures of a noble gas are applied externally is measured in relation to the geometric volume of the sample. The open cell content was determined making no correction for surfaces which had become cut open during preparation of the sample. The compressive strength of the foam was ascertained by way of determining pressure-distortion curves (measuring the force per unit of sample area at a deformation of 15%).

The individual measured values are reported in the Table below. In order to demonstrate that sample bodies which are identical to within the tolerance give the same measured values, the compressive strength and the open cell content were in each case determined on all of the sample bodies.

| Sample disk | Density | | Compressive strength | | Open cell content | |
|---|---|---|---|---|---|---|
| | Average [g/l] | Standard deviation [g/l] | Average [MPa] | Standard deviation [MPa] | Average [%] | Standard deviation [%] |
| 3 cm | 36.0 | 0.32 | 0.30 | 0.006 | 26 | 3.1 |
| 4 cm | 33.9 | 0.34 | 0.29 | 0.015 | 25 | 2.8 |
| 5 cm | 33.8 | 0.32 | 0.28 | 0.008 | 29 | 3.4 |
| 6 cm | 32.9 | 0.30 | 0.29 | 0.006 | 30 | 2.0 |
| 7 cm | 32.5 | 0.29 | 0.27 | 0.015 | 32 | 1.6 |
| 8 cm | 32.0 | 0.31 | 0.24 | 0.018 | 31 | 1.4 |
| 9 cm | 31.2 | 0.22 | 0.23 | 0.014 | 30 | 2.1 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method for evaluating a polyurethane-forming formulation comprising:

a) introducing a polyurethane foam-forming reaction mixture into a container made of an air-tight material, b) allowing the reaction mixture to foam in the optionally sealed container, c) dividing the container and its polyurethane foam contents into one or more disks having a predetermined thickness, d) removing from at least one disk produced in step c) a plurality of cylindrical sample bodies which are substantially identical in dimensions and density, and e) measuring, in parallel, a physical property of the polyurethane foam sample body produced in step d).

* * * * *